United States Patent [19]

Fukuhara et al.

[11] Patent Number: 5,081,321
[45] Date of Patent: Jan. 14, 1992

[54] PREPARATION OF ISOPROPANOL

[75] Inventors: Hiroshi Fukuhara, Ichihara; Fujihisa Matsunaga, Wakayama; Yasunori Shibuta, Ichihara; Toshihiro Tachi, Kuga, all of Japan

[73] Assignee: Mitsui Petrochemical Industries, Ltd., Tokyo, Japan

[21] Appl. No.: 464,315

[22] Filed: Jan. 12, 1990

[30] Foreign Application Priority Data

Jan. 17, 1989 [JP] Japan ............................. 1-8044
Oct. 26, 1989 [JP] Japan ............................. 1-279059

[51] Int. Cl.⁵ ...................... C07C 29/145; C07C 31/10
[52] U.S. Cl. ................................................. 568/881
[58] Field of Search ........................................ 568/881

[56] References Cited

U.S. PATENT DOCUMENTS

| 3,880,940 | 4/1975 | Baer et al. | 560/881 |
| 4,288,640 | 9/1981 | Schuster et al. | 568/855 |
| 4,361,705 | 11/1982 | Marcelin et al. | 568/881 |

FOREIGN PATENT DOCUMENTS

| 756877 | 3/1971 | Belgium | 568/881 |
| 2012729 | 1/1987 | Japan | 568/881 |
| 62-12729 | 6/1987 | Japan . | |
| 62-77338 | 9/1987 | Japan . | |
| 1002372 | 8/1965 | United Kingdom | 568/881 |
| 1182797 | 3/1970 | United Kingdom | 568/881 |
| 1183637 | 3/1970 | United Kingdom | 568/881 |

OTHER PUBLICATIONS

G. Tosun, Industrial & Engineering Chemistry—Process Design and Development, vol. 23, No. 1, Jan. 1984, pp. 29-32.

Primary Examiner—J. E. Evans
Attorney, Agent, or Firm—Nixon & Vanderhye

[57] ABSTRACT

Isopropanol is prepared through catalytic hydrogenation of acetone by feeding hydrogen gas and acetone liquid into a reactor having a fixed catalyst bed from its top to form a cocurrent gas/liquid downflow while maintaining the catalyst bed in a trickle bed state. This process can produce isopropanol at a high reaction rate in high yields using a simple reactor.

4 Claims, 1 Drawing Sheet

- ISOPROPANOL / NITROGEN GAS (50°C)
- REFERENCE (GURAY TOSUN)
- ISOPROPANOL / NITROGEN GAS (21°C)
- DIISOPROPYL ETHER / NITROGEN GAS
- × WATER / NITROGEN GAS

- ● ISOPROPANOL / NITROGEN GAS (50°C)
- ⊙ REFERENCE (GURAY TOSUN)
- ⊗ ISOPROPANOL / NITROGEN GAS (21°C)
- ○ DIISOPROPYL ETHER / NITROGEN GAS
- × WATER / NITROGEN GAS

PREPARATION OF ISOPROPANOL

This invention relates to the preparation of isopropanol which is a very useful intermediate in organic synthesis as well as a commercially important solvent.

BACKGROUND OF THE INVENTION

One currently widespread approach for the preparation of isopropanol is hydration of propylene. Although it is an old technique to hydrate olefins in the presence of conc. sulfuric acid catalyst, corrosion by sulfuric acid is a problem.

Other currently widespread approaches include hydration in gas/liquid mixed phase using strongly acidic ion-exchange resins, hydration in gas phase using strongly acidic solid acid catalysts, and hydration by gas phase catalytic reaction using catalysts having heteropoly-acids or inorganic acids carried thereon.

It was also well known from the past to hydrogenate the carbonyl group of acetone to prepare isopropanol. Included are reduction using such reagents as lithium aluminum hydride and sodium boron hydride and catalytic reduction using hydrogen gas.

Several new proposals were made in recent years as disclosed in Japanese Patent Application Kokai Nos. 12729/1987 and 77338/1987.

At present, synthesis of isopropanol by hydrogenation of acetone does not commercially work in practice. As compared with the direct hydration of propylene, this route of synthesizing isopropanol from acetone resulting from oxidation of propylene requires one extra step and is unreasonable from a process aspect.

Now acetone is produced in great amounts as a by-product in the phenol manufacture by the cumene process. The acetone feed becomes surplus in industrial supply and draws attention as a drawback of the cumene process. Although acetone found a major use as a starting material to produce methyl methacrylate, the demand for acetone is reduced by the recent change-over of the starting material to produce methyl methacrylate to another material. It thus becomes necessary to ensure the economy of the cumene process to produce phenol by making efficient use of the surplus acetone by-product. One possible approach is to convert acetone into its derivative, that is isopropanol which is of great industrial value. This approach will aid in establishing the economy of the cumene process to produce phenol.

A variety of methods were known for the preparation of isopropanol from acetone as previously described. Regarding catalytic hydrogenation, however, only an unexpectedly small number of proposals are found. Industrial cost efficient production of isopropanol is a key factor for the feasibility of an isopropanol preparing process particularly when considered from the standpoint of assisting in establishing the economy of the phenol preparing cumene process as intended in the present invention. Industrial isopropanol production has not been well established in this sense.

SUMMARY OF THE INVENTION

An object of the present invention is to establish an industrial process for preparing isopropanol from acetone.

We made efforts in developing an economically most advantageous process. In order to carry out hydrogenation of acetone into isopropanol in a cost efficient manner, it is crucial that (1) the reactor used is of simple structure, (2) the reaction rate is high enough to provide a large amount of product through a moderately small reactor, and (3) isopropanol is produced in high yields. Based on these considerations, we have reached the present invention.

The present invention provides a process for preparing isopropanol by catalytic hydrogenation of acetone. The feature of the invention is to feed hydrogen gas and acetone liquid into a reactor having a fixed catalyst bed from its top to form a cocurrent gas/liquid downflow while maintaining the catalyst bed in a trickle bed state.

BRIEF DESCRIPTION OF THE DRAWING

The only figure.

DETAILED DESCRIPTION OF THE INVENTION

Figure 1:
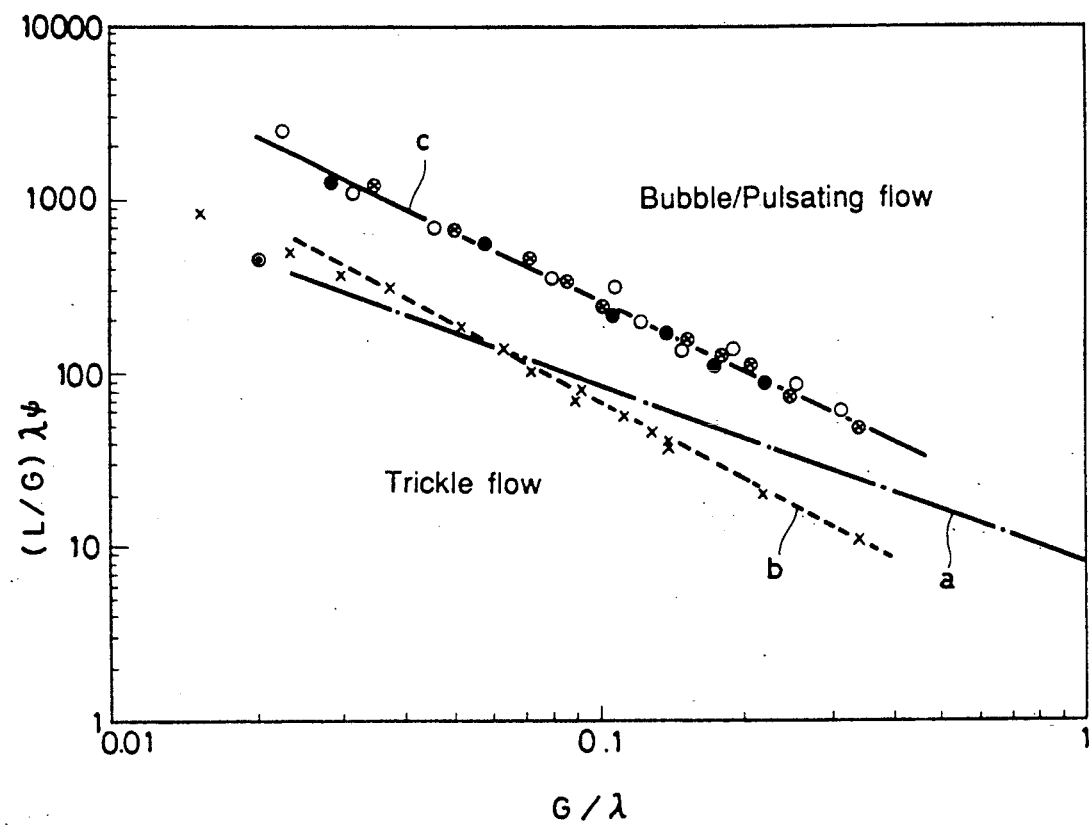
FIG. 1 is a diagram showing gas-liquid flow regimes.

For hydrogenation of acetone into isopropanol in a fixed bed system according to the invention, Raney nickel catalysts are most often used. Other catalysts known for hydrogenation may also be used, for example, copper base catalysts such as copper-chromium, Raney copper, and copper-zinc; nickel base catalysts such as reduced nickel catalysts prepared by carrying nickel oxide on a diatomaceous earth, alumina or silica support and tailoring it through a reducing treatment; and platinum group catalysts such as platinum, palladium, ruthenium, and rhodium as well as the foregoing catalysts on activated carbon and alumina supports.

Reaction may preferably be effected at a temperature of from room temperature to 200° C. although an industrial reaction rate is achieved at a reaction temperature of from 35 to 150° C. Too higher reaction temperatures will induce excess hydrogenation decomposition of acetone, resulting in reduced yields of isopropanol.

The reaction pressure may be in the range of from atmospheric pressure to 80 kg/cm$^2$, more preferably from 2 to 50 kg/cm$^2$.

In the practice of the invention, hydrogen gas and acetone reactant are preferably fed in such a proportion that 1.0 to 10 mol, more preferably 1.2 to 5 mol of hydrogen is present per mole of acetone.

The hydrogenation may be effected in the presence or absence of a reaction medium. The solvent, if used, may be selected from alcohols such as methanol, ethanol, propanol, and butanol. Isopropanol which is a hydrogenation product of acetone is also a useful solvent. Also useful are ethylene glycol, propylene glycol, diethylene glycol, triethylene glycol and the like. Other useful solvents include ethers such as diisopropyl ether, dibutyl ether, ethylene glycol dimethyl ether, diglyme, triglyme, etc.; aprotic polar solvents such as dimethylformamide, dimethylacetamide, acetonitrile, dimethylsulfoxide, etc.; and saturated hydrocarbons such as hexane, heptane, cyclopentane, cyclohexane, etc. Water is also a useful solvent for the hydrogenation of the invention.

It is essential in the practice of the invention to employ a fixed bed reaction system having a granular or particulate catalyst incorporated therein. The fixed bed system is easy to separate the reaction mixture from the catalyst and uses a reactor of simple structure.

In carrying out the present hydrogenation reaction in a fixed bed system, the direction of reactant liquid and hydrogen gas flows and the state of the catalyst are critical. It is critical to provide a cocurrent liquid/gas downflow relative to the fixed bed catalyst and to maintain the catalyst bed in a trickle bed state. By the term "trickle bed state" it is meant that the reactant liquid trickles along the surface of the catalyst which is packed in an atmosphere full of hydrogen gas. Therefore, no significant movement will be observed in appearance in the catalyst bed, as if standing still in spite of the presence of liquid/gas flow.

However, once the amounts of liquid and gas passing through the catalyst bed increase, the liquid flow becomes irregular and formation of a pool of liquid is observed at the bottom of the catalyst bed. As the amount of such pools of liquid increases, liquid and gas start to flow down in a form of mixture. Such a state of downflow is called bubble flow. When the bubble flow becomes more severe, the liquid/gas downflow reaches another state which is called pulse flow. A violent movement of liquid/gas flow will be observed in the state of pulse flow, because the phase of liquid/gas mixture is divided into two zones, one zone with higher ratio of liquid to gas and the other being rich in gas, and these two zones flow down by turns.

Changes in the flow mode in the catalyst bed from a trickle flow state to a bubble flow state and still more to a pulse flow state can be recognized clearly as the movement of the differential pressure between the upper and lower parts of the catalyst bed. In other words, changes in the differential pressure between the upper and lower parts of the catalyst bed can not be detected in the state of trickle flow, but become evident as the liquid/gas downflow enters the bubble flow state. Though degree of changes in the differential pressure varies depending on the mix ratio of liquid and gas, the liquid/gas downflow is in the state of bubble flow when a water manometer shows $\pm 1$ -2 mm of changes in the differential rate and is absolutely in the state of pulse flow when the changes exceed $\pm 5$ mm.

Reaction in a trickle bed state is effective for gas-liquid-solid related reaction, particularly such reaction in which gas largely participates. Since the present hydrogenation is a reaction in which hydrogen molecules adsorbed onto the catalyst react with acetone to form isopropanol, location of the catalyst in a hydrogen gas atmosphere facilitates adsorption of hydrogen molecules to the catalyst. In the case of normal hydrogenation not in a trickle bed state, hydrogen molecules are once dissolved in the reactant liquid and then adsorbed to the catalyst so that the rate of adsorption of hydrogen to the catalyst is slower than in the trickle bed state. Although the magnitude of hydrogen adsorption rate does not largely affect the overall reaction rate of a process in which hydrogenation is slow, the hydrogen adsorption rate has a critical influence on the present hydrogenation process.

Therefore, the present hydrogenation reaction must be conducted in a trickle bed state in order to achieve the objects of the invention.

The setting for establishing a trickle bed state in the catalyst bed during hydrogenation reaction is given by the following case (i) or (ii). (i) Hydrogen gas and acetone liquid are fed to form a cocurrent downflow through a catalyst bed in such a molar ratio to provide a hydrogen excess state, more particularly to ensure that the molar ratio of hydrogen gas to acetone reactant is larger than unity.

The following equation should be met.

$$\frac{B}{Ax\frac{\alpha}{100}} > 1 \tag{1}$$

wherein B is moles of hydrogen, A is moles of acetone, and $\alpha$ is a percent conversion of acetone. (ii) Hydrogen gas and acetone liquid are controlledly fed in such flow rates as to provide a gas-liquid flow in trickle flow state using the flow map proposed by Guray Tosun.

FIG. 1 shows the results of visual observation of flow for gas/liquid systems through a packed bed wherein the flow velocity of a gas/liquid downflow is varied.

Line a in FIG. 1 is a flow map depicted as FIG. 6 in Guray Tosun "A Study of Cocurrent Downflow of Nonfoaming Gas-Liquid Systems in a Packed Bed," Ind. Eng. Chem. Process Des. Dev., Vol. 23, No. 1 (1984), pages 29-35. Lines b and c in FIG. 1 are the flow map to show the results obtained in the following experiments by the present invention. In Guray Tosum, the boundary between trickle flow and bubble flow is depicted by a line marked "a". The gas and liquid feeds are chosen so as to fall in the range in FIG. 1 defined by the following relationships.

$$\log\left(\frac{L}{G}\lambda\psi\right) < -1.03\log\left(\frac{G}{\lambda}\right) + \log 8 \tag{2}$$

$$0.01 < \left(\frac{G}{\lambda}\right) < 2.0 \tag{3}$$

In the formulae, G is a superficial mass velocity of hydrogen gas in kg/m²s,

L is a superficial mass velocity of acetone liquid in kg/m²s, $$\psi = \left(\frac{\sigma_w}{\sigma_L}\right)\left[\left(\frac{\mu_L}{\mu_w}\right)\left(\frac{\rho_w}{\rho_L}\right)^2\right]^{\frac{1}{3}}$$

$$\lambda = \left[\left(\frac{\rho_G}{\rho_w}\right)\left(\frac{\rho_L}{\rho_{air}}\right)\right]^{\frac{1}{2}}$$

$\rho_G$ is a density of hydrogen gas in g/cm³,
$\rho_L$ is a density of acetone liquid in g/cm³,
$\rho_w$ is a density of water in g/cm³,
$\rho_{air}$ is a density of air in g/cm³,
$\sigma_w$ is a surface tension of water in dyn/cm,
$\sigma_L$ is a surface tension of acetone liquid in dyn/cm,
$\mu_L$ is a viscosity of acetone liquid in centipoise, and
$\mu_w$ is a viscosity of water in centipoise.

It is to be noted that the gas superficial mass velocity used herein is the amount of gas supplied into a packed bed catalyst through the upper side of a reaction column containing the catalyst, and this gas flow rate (1/hr) measured by using a gas flowmeter is then converted to a value of mass velocity per unit cross section area of the reaction column (kg/m²·sec).

Liquid superficial mass velocity is calculated in the same manner based on the liquid flow rate.

The gas and liquid superficial mass velocities are defined by the following relationships.

Gas superficial mass velocity (kg/m² · sec) =

$$\text{Liquid superficial mass velocity (kg/m}^2 \cdot \text{sec)} = \frac{\text{liquid supply (l/hr)} \times \text{liquid density (kg/l)}}{\text{cross section of reaction column (m}^2) \times 3600 \text{ (sec/hr)}}$$

According to a result of experiments performed by the inventors of the present invention, line b shown in FIG. 1 is obtained as the boundary between trickle flow and bubble flow when a water/nitrogen gas system is used as the gas/liquid downflow system in the experiments. The line b coincides closely with the line a described by Guray Tosun.

However, results shown as line c in FIG. 1 are obtained when an isopropanol/nitrogen gas system (50° C.), an isopropanol/nitrogen gas system (21° C.) and a diisopropyl ether/nitrogen gas system are used as the experimental system which is close to the process of the present invention for the preparation of isopropanol. Though the line c is almost parallel with the line a described by Guray Tosun, relationships having different constants from the line a described by Guray Tosun are obtained from the line c as follows.

$$\log\left(\frac{L}{G}\psi\right) < A \log\left(\frac{G}{\lambda}\right) + \log B \tag{4}$$

wherein $A = -1.35$ and $B = 11.6$ $$0.01 < \left(\frac{G}{\lambda}\right) < 2.0 \tag{5}$$

In consequence, it was found that a state of trickle flow can be obtained by supplying certain amounts of gas and liquid which satisfy these relationships (4) and (5).

With gas and liquid feeds outside the above-defined range, the gas/liquid flow through the catalyst bed departs from a trickle flow as seen from FIG. 1, resulting in either a foaming state wherein hydrogen gas flows down through a liquid layer formed in the catalyst bed or a pulsating state wherein gas and liquid form a pulsating flow. In either state, not only hydrogenation does not smoothly proceed, resulting in reduced efficiencies or yields, but also a drastically varying, significant differential pressure develops across the catalyst bed, prohibiting stable continuous reaction.

Also a vigorous pulsating flow will vibrate the fixed catalyst bed, causing a fracture of the catalyst. The catalyst fracture results in a reduced catalyst life and gives rise to some troubles like clogging because catalyst fragments will flow out of the reactor to a subsequent step.

It is thus critical for the present hydrogenation of acetone into isopropanol to maintain a trickle bed state in the catalyst bed.

EXAMPLE

Examples of the present invention are given below by way of illustration and not by way of limitation.

EXAMPLE 1

A stainless steel vertical reactor column having an inner diameter of 25.4 mm (1 inch) and a length of 500 mm was loaded at a mid-portion with 100 grams (50 ml) of a lumpy (beads with length 6–7 mm and breadth 4–5 mm) Raney nickel alloy (50/50 Ni/Al, R–20L manufactured by Nikko Rika K.K.). The reactor was filled with water. The Raney nickel catalyst was then developed by gradually pumping 1280 grams of an aqueous sodium hydroxide developer into the reactor from its bottom, the developer being prepared by dissolving 128 grams of sodium hydroxide in water and adjusting to a concentration of 10% by weight. The catalyst development was accompanied by an exothermic reaction so that the temperature of the reactor interior rose. The feed rate of the sodium hydroxide developer was adjusted and the reactor was temperature controlled by air cooling or the like so that the interior temperature did not exceed 50° C. The used developer exiting from the reactor top was fed back to the mother sodium hydroxide developer for recycle use. The amount of hydrogen gas given off with the progress of development was measured by a gas meter. Pumping of the alkaline developer was continued until a substantial cessation of hydrogen gas emission (approximately 20 hours). The total amount of hydrogen gas emission indicated that the rate of development of the catalyst was 50%. At the end of catalyst development, the pump feed was replaced by water to wash the reactor interior with water. Water washing was continued until the outflow from the reactor became neutral. At the end of water washing, the pump feed was replaced by isopropanol to purge the reactor interior with isopropanol.

Heating of the reactor was started. When the interior temperature reached 100° C., reaction was started by feeding 39.5 gram/hour of acetone and 37.2 liter/hour of hydrogen into the reactor from the top. A pressure of 20 kgf/cm$^2$ was maintained in the reactor. The reaction mixture exiting from the reactor bottom was separated into the reaction solution and hydrogen gas by a gas/liquid separator. There were discharged 39.8 gram/hour of reaction solution and 16.4 liter/hour of exhausted hydrogen gas.

Continuous reaction was conducted for 9 hours by feeding acetone and hydrogen. At this point, the reaction solution and the exhaust gas were analyzed by gas chromatography, finding that 0.1% by weight of acetone remained in the reaction solution. The balance of the reaction solution was solely isopropanol. The conversion of acetone was 99.9% and the yield of isopropanol was 99.9%.

EXAMPLE 2

The procedure of Example 1 was repeated except that the flow rates of acetone and hydrogen were changed to 78.7 gram/hour and 64.4 liter/hour, respectively. The results included an acetone conversion of 98.4% and an isopropanol yield of 98.4%.

COMPARATIVE EXAMPLE 1

The procedure of Example 1 was repeated except that acetone and hydrogen were introduced into the reactor from the bottom. The results included an acetone conversion of 8.6% and an isopropanol yield of 88.6%.

EXAMPLE 3

The procedure of Example 1 was repeated except that the reaction temperature was lowered to 80° C. The results included an acetone conversion of 99.7% and an isopropanol yield of 99.7%.

EXAMPLE 4

The procedure of Example 1 was repeated except that the reaction pressure was changed to 15 kgf/cm². The results included an acetone conversion of 98.6% and an isopropanol yield of 98.6%.

EXAMPLE 5

The procedure of Example 1 was repeated except that the reaction pressure was changed to 10 kgf/cm². The results included an acetone conversion of 95.2% and an isopropanol yield of 95.2%.

EXAMPLE 6

A stainless steel vertical reactor column having an inner diameter of 25.4 mm (1 inch) and a length of 1,100 mm was loaded at a mid-portion with 200 ml of a lumpy Raney nickel catalyst (beads with length 6-7 mm and breadth 4-5 mm, rate of development 60%). The reactor was filled with isopropanol. The temperature of the reactor interior was raised by passing warm water at 70° C. through a reactor jacket. When the interior temperature reached 70° C., acetone, isopropanol and hydrogen were introduced into the reactor from its top through respective inlet tubes connected thereto. The flow rates of acetone, isopropanol and hydrogen were adjusted to 400 ml/hour, 400 ml/hour and 247 liter(standard state)/hour, respectively. The reactor interior temperature rose to 85° C. after the start of hydrogenation while the warm water through the reactor jacket was maintained at 70° C. at the inlet.

With the start of feeding of the reactants, the reaction product and excess hydrogen gas exited the reactor at the bottom outlet. While the reactor interior pressure was maintained at 20 kg/cm² by means of a pressure regulator valve at the bottom outlet, the gas/liquid mixture was taken out of the reactor and introduced into a reservoir where the excess hydrogen was separated from the reaction product. A portion of the reaction product was separated and recycled as a substitute for the isopropanol feed to the reactor.

Continuous reaction was conducted under conditions: acetone feed 400 ml/hour, reaction solution recycle feed 400 ml/hour, hydrogen feed 247 liter(standard state)/hour, a reactor interior pressure of 20 kg/cm², and a reactor interior temperature of 85° C. The reaction product was periodically sampled out for gas chromatography analysis to evaluate the results of hydrogenation. Consistent reaction results were obtained including an acetone conversion of 98.0% and an isopropanol selectivity of 99.9%.

EXAMPLE 7

A stainless steel vertical reactor column having an inner diameter of 38.4 mm and a length of 4,800 mm was loaded with 2,500 ml of the same lumpy Raney nickel catalyst as used in Example 6. The reactor was filled with isopropanol. The reactor at the top had inlet ports for the reactant and hydrogen. A pressure gauge was provided for measuring the differential pressure between the top and the bottom of the reactor. The reactor at the bottom had an outlet port in flow communication with a reservoir for the reaction mixture. The reservoir was adapted to separate excess hydrogen gas from the reaction solution.

The reaction solution was divided into two portions. The first portion was taken out of the reaction system as a product. The second portion was fed back by means of a recycle pump to the reactor top where it was combined with acetone to form a feed mixture for reaction. In a line for recycling the reaction solution second portion was provided a heat exchanger. The reactor interior temperature was then maintained at a predetermined temperature by controlling the jacket temperature of the heat exchanger.

The isopropanol in the reactor was started to flow along with the pumped flow from the recycle line and at the same time, feeding of hydrogen gas was started. Feeding of acetone was also started through an acetone feed line connected to the inlet port of the reactor.

The following reaction conditions were set: acetone feed 3 liter/hour, reaction solution recycle feed 24 liter/hour, and hydrogen feed 1850 liter(standard state)/hour. The reactant preheated to 77° C. was fed along with hydrogen gas while maintaining a reactor interior pressure of 18 kg/cm². There was discharged a reaction mixture at 113° C. from the outlet of the reactor. After the reaction conditions became stable, the reaction product was analyzed, finding an acetone conversion of 99.8% and an isopropanol selectivity of 99.9%.

The differential pressure between the top and the bottom of the reactor was always maintained at 120 mm in water manometer.

The parameters used in this hydrogenation are shown below.

$G$, hydrogen gas superficial mass velocity: 0.037 kg/m²s $L$, isopropanol liquid superficial mass velocity: 5.053 kg/m²s $\Psi = 4.374$ $\lambda = 0.945$ $\rho_G$, hydrogen gas density: 1.472 kg/m³ (75° C., 20.5 kg/cm²)

$\rho_L$, isopropanol liquid density: 0.73 g/cm³ (75° C.)

$\rho_w$, water density: 0.998 g/cm³ (20° C.)

$\rho_{air}$, air density: 1.205 kg/m³ (20° C., 1 atm)

$\sigma_w$, water surface tension: 72.6 dyn/cm (20° C.)

$\sigma_L$, isopropanol liquid surface tension: 17.3 dyn/cm (75° C.)

$\mu_L$, isopropanol liquid viscosity: 0.6 cp (75° C.)

$\mu_w$, water viscosity: 0.99 cp (20° C.)

$$\log\left(\frac{L}{G}\lambda\psi\right) = 564$$

$$\frac{G}{\lambda} = 0.039$$

COMPARATIVE EXAMPLE 2

The procedure of Example 7 was repeated except that the reaction conditions were set: acetone feed 6 liter/hour, reaction solution recycle feed 48 liter/hour, and hydrogen feed 3710 N-liter/hour.

The differential pressure between the top and the bottom of the reactor was 550 mm in water column with drastic fluctuations of ±10 mm.

The reaction product discharge from the reactor showed a drastic pulsating flow synchronous with the fluctuations of differential pressure across the reactor.

The concentration of acetone remaining in the reaction product also varied and as a result, the acetone conversion varied between 93.4% and 94.7%.

It was difficult to continue stable hydrogenation if the gas/liquid system in the reactor deviated from a trickle bed state.

There has been described a process for preparing isopropanol by catalytic hydrogenation of acetone in a vertical reactor having a fixed catalyst bed wherein hydrogen gas and acetone liquid are introduced into the reactor from its top to form a cocurrent gas/liquid downflow while maintaining a trickle flow through the catalyst bed.

The process of the invention can produce isopropanol from acetone in a simplified reactor without a need for careful operation and cumbersome catalyst separation. The present process is of great industrial value since isopropanol can be produced at a high reaction rate in high yields.

Although some preferred embodiments have been described, many modifications and variations may be made thereto in the light of the above teachings. It is therefore to be understood that within the scope of the appended claims, the invention may be practiced otherwise than as specifically described.

I claim:

1. A process for preparing isopropanol by the catalytic hydrogenation of acetone, comprising feeding hydrogen gas and acetone liquid into a reactor having a fixed catalyst bed from its top to form a cocurrent gas/liquid downflow while maintaining the catalyst bed in a trickle bed state, wherein the hydrogen gas and the acetone liquid are fed in such a molar ratio to meet the following equation:

$$\frac{B}{A \times \frac{a}{100}} > 1 \quad (1)$$

wherein B is moles of hydrogen, A is moles of acetone, and is a percent conversion of acetone and wherein the hydrogen gas and the acetone liquid are fed at a superficial mass velocity to meet the following equations:

$$\log\left(\frac{L}{G}\lambda\psi\right) < -1.35\log\left(\frac{G}{\lambda}\right) + \log 11.6$$

$$0.01 < \left(\frac{G}{\lambda}\right) < 2.0$$

wherein G is a superficial mass velocity of hydrogen gas in kg/m$^2$s, L is a superficial mass velocity of acetone liquid in kg/m$^2$s, $$\psi = \left(\frac{\sigma_w}{\sigma_L}\right)\left[\left(\frac{\mu_L}{\mu_w}\right)\left(\frac{\rho_w}{\rho_L}\right)^2\right]^{\frac{1}{3}}$$

$$\lambda = \left[\left(\frac{\rho_G}{\rho_w}\right)\left(\frac{\rho_L}{\rho_{air}}\right)\right]^{\frac{1}{2}}$$

$\rho_G$ is a density of hydrogen gas in g/cm$^3$,
$\rho_L$ is a density of isopropanol liquid in g/cm$^3$,
$\rho_w$ is a density of water in g/cm$^3$,
$\rho_{air}$ is a density of air in g/cm$^3$,
$\sigma_w$ is a surface tension of water in dyn/cm,
$\sigma_L$ is a surface tension of isopropanol liquid in dyn/cm,
$\mu_L$ is a viscosity of isopropanol liquid in centipoise, and
$\mu_w$ is a viscosity of water in centipoise.

2. The process of claim 1 wherein said catalyst is a Raney nickel catalyst.

3. The process of claim 1 wherein the reactive system is continuous system and isopropanol liquid is fed to the reaction system in addition to the hydrogen gas and acetone liquid.

4. The process of claim 3 wherein the isopropanol fed to the reaction system is the reaction product.

* * * * *